United States Patent [19]

Borsotti et al.

[11] Patent Number: 5,527,892
[45] Date of Patent: Jun. 18, 1996

[54] PROCESS FOR PREPARING APG'S

[75] Inventors: Giampiero Borsotti, Novara; Tullio Pellizzon, Paderno Dugnano, both of Italy

[73] Assignees: Eniricerche S.p.A.; Enichem S.p.A., both of Milan, Italy

[21] Appl. No.: 213,702

[22] Filed: Mar. 16, 1994

[30] Foreign Application Priority Data

Mar. 19, 1993 [IT] Italy ................... MI93A0518

[51] Int. Cl.⁶ .............. C07H 15/00; C07H 1/06; C07H 3/00; C08B 37/00
[52] U.S. Cl. .............. 536/18.6; 536/124; 536/126; 536/127; 536/123.1; 252/174.17
[58] Field of Search ................... 536/18.6, 124, 536/126, 127; 424/70; 252/174.17, DIG. 5, DIG. 13, DIG. 14

[56] References Cited

U.S. PATENT DOCUMENTS

| 4,223,129 | 9/1980 | Roth et al. ................ 536/4 |
|---|---|---|
| 4,393,203 | 7/1983 | Mao et al. ................ 536/124 |
| 4,713,447 | 12/1987 | Letton ................ 536/18.6 |
| 4,950,743 | 8/1990 | McCurry, Jr. et al. ........ 536/18.6 |
| 5,037,992 | 8/1991 | Ward et al. ................ 558/36 |
| 5,266,690 | 11/1993 | McCurry, Jr. et al. ........ 536/18.6 |

FOREIGN PATENT DOCUMENTS

| 0132046 | 1/1985 | European Pat. Off. . |
|---|---|---|
| 0132043 | 1/1985 | European Pat. Off. . |
| 0570056 | 11/1993 | European Pat. Off. . |
| WO90/07516 | 7/1990 | WIPO . |

Primary Examiner—Douglas W. Robinson
Assistant Examiner—Howard C. Lee
Attorney, Agent, or Firm—Oblon, Spivak, McClelland, Maier & Neustadt

[57] ABSTRACT

An improved method for synthesizing alkylpolyglucosides comprising reacting a glycoside with a long-chain alcohol in the presence of a novel type of catalyst, constituted by an alkali or aryl sulfonic acid, wherein the sulfonic group is sterically hindered. Using these catalysts, a raw product is obtained which is practically free from byproducts. The resulting alkyl polyglucosides are completely biodegradable surfactants and can be used to formulate detergents.

12 Claims, No Drawings

PROCESS FOR PREPARING APG'S

The present invention relates to an improved process for synthetizing alkylpolyglucosides.

In particular, the present invention relates to a process for synthetizing alkylpolyglucosides by using a novel catalyst, which is a sterically hindered sulfonic acid, which allows a better selectivity to the product, and therefore, a reaction raw product which is practically free from undesired byproducts, to be obtained.

Alkylpolyglucosides are a class of substances constituted by a chain of ring structures from a sugar linked to each other by glucosidic linkages; the last ring of the glucosidic chain is acetalized with an alcohol. The general structure of alkylpolyglucosides is represented by the formula:

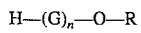

$$H-(G)_n-O-R$$

wherein G represents a glucosidic unit, R is the corresponding residue to the alcohol used in order to form the glucosidic acetal and n is the polymerization degree, i.e., the number of mutually linked glucosidic units.

Particularly important from an industrial viewpoint are those alkylpolyglucosides in which n is comprised within the range of from 1 to 5, and R is the residue of an aliphatic, (either straight or branched) long-chain alcohol. In fact, these types of alkylpolyglucosides are non-ionic surfactants which may find uses in the normal sectors of use of surfactants, and, in particular, in the detergency field. In the following, with the characters "APG", these particular alkylglucosidic oligomers are referred to, in short form, The value of n can be controlled by varying the molar ratio of alcohol to saccharide in the APG preparation reaction: in fact, when this ratio is increased, APG's with a lower average value of n are obtained. According to an alternative procedure, the separation can be carried out of produced APG's at the end of the production cycle, as disclosed in detail in following.

Alkylpolyglucosides offer, as compared to traditional surfactants, two important advantages: first of all, they can be obtained from renewable natural sources, essentially constituted by starch and coconut oil; secondly, alkylpolyglucosides are 100% biodegradable; consequently, the industrial interest in these compounds is high and has increased during the past few years.

The preparation of APG's has been studied for a number of years, and several synthesis routes are available, starting from different reactant combinations.

A first possibility is the direct synthesis by starting from the sugar and the alcohol (or alcohols mixture) which constitute the end product, with the alcohol being used in a stoichiometrical excess. According to an alternative synthetic route, the source of the glucosidic moiety of the molecule is constituted by starch obtained from cereals. In this case, the polysaccharide is generally firstly depolymerized with lower alcohols (methyl alcohol or, more commonly, butyl alcohol), in the presence of an acid as a catalyst; in this way, a blend of APG's with a short-chain R moiety is obtained. This blend is then treated under vacuum with the long-chain alcohol, in the presence of an acid as the catalyst, in order to exchange the alcoholic moiety: this last reaction is referred to as "transacetalization", and is favored by the removal, by evaporation, of the lower alcohol which is formed, which is lower boiling than the long-chain alcohol; in this case too, the process is carried out in the presence of an excess of long-chain alcohol over the stoichiometric amount.

In both of the above cases (either direct APG synthesis, or by transacetalization), an acidic catalyst should be used, the purpose of which is of favoring the reactions which interest the glucosidic bond. The used acids for this purpose in the industrial processes are mineral acids, such as, e.g., $H_2SO_4$, HCl, $H_3PO_4$ or $BF_3$, or, more commonly, sulfonic acids, or salts thereof. The used class of sulfonic acids is very wide and comprises, e.g., ortho-, meta- and para-toluenesulfonic acid, alkylbenzenesulfonic acid, secondary alkylsulfonic acids, sulfonic resins, alkylsulfates, alkylbenzenesulfonates, alkylsulfonates or sulfosuccinic acid. Some examples of the use of these acids are reported in following patents: DE 3,723,826; DE 3,842,541; DE 3,900,590; U.S. Pat. No. 4,950,743; EP 357,969; U.S. Pat. No. 4,223,129; U.S. Pat. No. 4,393,203; all of which relate to the use of para-toluenesulfonic acid (PTSA), which was the most widely used for long time; WO 90/07516, which relates to the use of dinonylnaphthalenesulfonic acid; U.S. Pat. No. 4,713,447, relevant to the use of dodecylbenzenesulfonic acid; DE 4,018,581 and WO 91/02742, relating to the use of sulfosuccinic acid; U.S. Pat. No. 3,219,656, in which sulfonic resins are used as the catalyst.

When the reaction is ended, the acidic catalyst is neutralized with a base. The most commonly used base is NaOH, however some patents claim the use of particular bases; for example, U.S. Pat. No. 4,713,447 discloses the use of alkoxides of alkali metals, alkaline-earth metals or aluminum or, according to an alternative route, of salts of these same metals with organic acids.

The last step of the process of production of APG's consists in separating said APG's from the excess of alcohol. This step is generally carried out by vacuum distillation, preferably thin film distillation, at temperatures of the order of 150°–180° C.; if SO desired, in order to facilitate it, this operation can be carried out in the presence of fluidizers, such as glycerol or glycols, or long-chain 1,2-diols ($C_{12}$–$C_{18}$), as disclosed in U.S. Pat. No. 4,889,925. Another procedure used in order to separate APG's from the excess of alcohol is the extraction with solvents, e.g., water, acetone or supercritical $CO_2$. Selecting either of both separation techniques also allows the "cut" of obtained APG's to be controlled: in fact, by distillation the whole blend of produced APG's is recovered, which is generally characterized by an average n value comprised within the range of from 1.2 to 1.7; if, on the contrary, one operates by solvent extraction, the lower molecular weight fractions, substantially constituted by alkylmonoglucosides, remain in solution, and in the solid material the highest molecular weight fractions, characterized by an average n value higher than 1.7 and generally comprised within the range of from 1.7 to 2.5, are concentrated; this separation method is disclosed, e.g., in U.S. Pat. No. 3,547,828 and in European patent application EP-A1-0 092 355.

A serious drawback common to all known processes for APG production is that polysaccharides are formed as byproducts: in fact, the most commonly used monosaccharides in APG production are polyalcohols with 5 or 6 alcoholic groups which can compete with the long-chain alkylic alcohol in the formation of the glucosidic bond. In the most common case, i.e., when one operates with glucose or a precursor thereof, this secondary reaction leads to the formation of polyglucose. This effect is undesired because, besides subtracting reactants from the main reaction, the resulting polyglucose is a solid product the presence of which, also in a low percentage, in the product blend, causes an increase in blend viscosity and the precipitation of products in jelly-like form. As a consequence, all the subsequent operations in APG production porduct, i.e., the separation of APG's from the raw reaction porduct, washing the product, recovering and possibly recycling alkylglucosides and unreacted alcohols, become extremely difficult.

In order to overcome this drawback, one might work with high alcohol/glucose ratios: unfortunately, this solution implies the use of large alcohol volumes, with the relevant safety problems and the oversizing of APG production facilities.

As a further possibility for limiting polyglucose formation, the control was proposed of the acidic catalyst: in fact, it was observed that the type of catalyst may have an influence on the composition of the raw reaction product. For example, when one operates with a molar ratio of alcohol:glucose of 2:1, with $H_2SO_4$ as the catalyst, a polyglucose level is obtained which is higher than 20%, whereas with PTSA this level is reduced to about 11%; according to EP patent 132,043, when as catalysts alkylsulfonic or benzenesulfonic acids are used, said level is further decreased down to 9.2%. In WO patent 90/07516, a novel, high-lipophilicity class of sulfonic acids are disclosed which, when one operates with a molar ratio of alcohol:glucose of 5:1, makes it possible the polyglucose content to be reduced down to 2.2%; unfortunately, such catalysts have a high cost.

In commonly owned Italian patent application MI 92A 001157,when a binary catalyst is used which is constituted by a weak base coupled with a strong organic acid, with a ratio of alcohol:glucose of 5:1, a level of polyglucose of 0.7% is obtained.

The present Applicant found now that a novel class of catalysts, consisting of sterically hindered sulfonic acid used alone, makes it possible the formation of polyglucose in the reaction of formation of APG's to be further reduced.

Therefore, the object of the present invention is a process for preparing alkylpolyglucosides of general formula (I):

wherein:
R is an either linear or branched, saturated or unsaturated alkyl radical having from 8 to 20 carbon atoms;
G is residue resulting from the removal of an $H_2O$ molecule from a monosaccharide, typically an hexose or a pentose having formula $C_6H_{12}O_6$ or $C_5H_{10}O_5$, respectively;
n is an integer comprised within the range of from 1 to 5;
said process comprising the reaction of an alcohol with a monosaccharide or an equivalent thereof, which may be an alkylglucoside, or a compound capable of generating in situ the monosaccharide, carried out in the presence of a catalyst consisting of a sulfonic acid in which the —$SO_3H$ is sterically hindered.

The sterically hindered sulfonic acid according to the present invention can be arylsulfonic acid defined by the following formula (II):

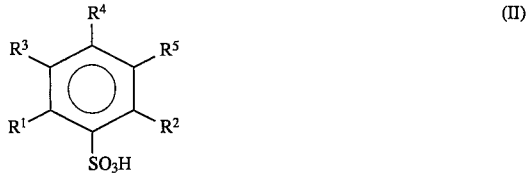

wherein $R^1$ and $R^2$, which may be the same or different from each other, can be:
an alkyl radical having from 1 to 4 carbon atoms;
a halogen selected from Cl, Br and I;
a residue selected from the group consisting of —$OR^6$, —$SR^7$, —$COOR^8$ moieties, wherein $R^6$, $R^7$ and $R^8$ are alkyl residues having from 1 to 4 carbon atoms;

and in which $R^3$, $R^4$ and $R^5$, which may be the same or different from each other, can be hydrogen, or may have any of the meanings as defined above for $R^1$ and $R^2$.

Examples of catalysts according to formula (II) are: 2,4,6-tri-methyl-benzene-sulfonic acid; 2,4,6-tri-ethyl-benzene-sulfonic acid; 2,4,6-tri-isopropyl- benzene-sulfonic acid; 2,4,6-tri-isobutyl-benzenesulfonic acid; 2,6-dicarboxy-benzene-sulfonic acid; 2,4,6-tri-ethoxy-benzene-sulfonic acid; 2,4,6-tri-chloro-benzene-sulfonic acid.

According to an alternative embodiment of the present invention, as sterically hindered sulfonic acid, there can be used those secondary alkylsulfonic acids as defined by the following formula (III):

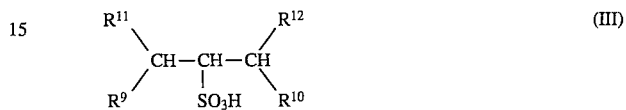

wherein $R^9$, $R^{10}$, $R^{11}$ and $R^{12}$, which may be the same or different from one another, may be any of the groups defined above for $R^1$ and $R^2$ and wherein the $R^{11}$ and $R^{12}$ moieties may possibly form, when taken together, an alkylenic residue having from 2 to 4 carbon atoms, which may be either substituted or unsubstituted.

Examples of catalyst according to formula (III) are: 3,5-diisopropylheptane-4-sulfonic acid, 2,6-dimethyl-3,5-diisopropyl-4-heptanesulfonic acid, 2,2,6,6-tetraethylcyclohexanesulfonic acid, 2,2,6,6-tetraisopropylcyclohexanesulfonic acid.

Preferred catalysts according to the present invention ape 2,4,6-triisopropylbenzenesulfonic acid and 2,4,6-triisobutyl-benzenesulfonic acid, from those corresponding to formula (II), and 2,6-dimethyl-3,5 -diisopropyl-4-heptanesulfonic acid and 2,2,6,6-tetraisopropylcyclohexanesulfonic acid, from those corresponding to formula (III).

The process according to the present invention comprises the reaction of a monosaccharide or an equivalent thereof, with a monohydroxy alcohol having from 8 to 20 carbon atoms, in the presence of the above disclosed acidic catalyst; said reaction is carried out at a temperature comprised within the range of from 110° to 130° C., under vacuum, with formed water being continuously removed.

Monosaccharides which can be advantageously used in the process according to the present invention are, e.g.: glucose, mannose, galactose, arabinose, xylose, ribose and the like; among these, glucose is preferred thanks to its low cost and wide availability.

The definition of "monosaccharide equivalent compound" encompasses both the alkyl glucosides of lower alcohols, such as, e.g., butyl glucosides; and higher sugars or saccharides which, under the reaction conditions can be hydrolized into monosaccharides, such as, e.g., starch, maltose, saccharose, lactose, and so forth. Among the preferred precursors for monosaccharides, we wish to mention here, e.g., those butyl polyglucosides which are obtained by alcoholysis of starch or corn syrup.

Suitable alcohols for the process according to the present invention are primary or secondary, either straight- or branched-chain saturated or unsaturated monohydroxy alcohols containing from 8 to 20 carbon atoms, and their mixtures.

Examples of alcohols are octanol, decanol, lauryl alcohol, myristyl alcohol, oleyl alcohol and alcohols from oxosynthesis having a linear:branched ratio of 45:55, such as LIAL 111®, LIAL 123®, LIAL 145®, or linear alcohol fractions obtained from these blends by fractional crystallization (ALCHEM 111®, ALCHEM 123®, ALCHEM 145®). It should be observed that the catalysts according to the present invention make using these blends which contain branched alcohols advantageous at industrial level: in fact, when these alcohols blends are used in order to produce APG's in the presence of catalysts known from the prior art, undesired conversion rates of glucose to polyglucose higher than 20% are obtained, whilst the catalysts according to the present invention make it possible this level to be reduced, in some cases, under 1%.

The alcohol is used in an excess amount over the stoichiometric value, and namely with a molar ratio of alcohol to monosaccharide comprised within the range of from 1 to 7 and preferably of from 1.5 to 3.3. The alcohol also acts as the reaction solvent.

The catalyst can be used in amounts comprised within the range of from 0.001 to 0.1 mols/mol of monosaccharide (or of an equivalent thereof), and preferably in amounts comprised within the range of from 0.001 to 0.01 mols/mol of monosaccharide.

The reaction can be carried out batchwise or, preferably, continuously.

At reaction end, the raw reaction product is mixed with a solvent in which APG's are insoluble, e.g., acetone. In the washing liquors, the excess of alcohols, alkylmonosaccharides and practically all of the catalyst remain, and the precipitate is constituted by the APG's. The separation of the precipitate can be carried out according to a known method, such as, e.g., decantation or centrifugation.

The advantages attained from the use of the catalyst according to the present invention are particularly evident in this step.

In fact, when the catalyst known from the prior art are used, when the reaction mixture is precipitated with solvent, a jelly-like APG precipitate is always obtained; all of the following precipitate separation and purification steps consequently are longer and more difficult. For example, when para-toluenesulfonic acid is used, a jelly-like product is obtained, the washing of which by filtration on porous frit filters requires filtration times of round 10 hours; furthermore, owing to the jelly-like nature of the product, the washing thereof is never complete and residues of alcohol and catalyst remain always intrapped inside the product.

On the contrary, when the catalysts according to the present invention are used, the content of polysaccharide is nearly completely removed and, upon solvent addition, an APG precipitate is obtained the washing of which by filtration on a porous frit filter requires only a 1-hour time, and in which at most traces, if any, of the other components of the raw reaction mixture remain intrapped. This feature is another important advantage of the process according to the present invention: in fact, the wash liquors can be combined with the liquid phase obtained from the previous step of APG separation from the raw reaction mixture; this liquid phase, which contains the alcohol, the alkylmonosaccharide and the catalyst, can be recycled into the reaction after solvent evaporation. In this way, the neutralization of the acidic catalyst with bases, which is carried out in a large number of processes according to the prior art, is no longer necessary. The loss of catalyst, caused by said catalyst remaining intrapped inside the APG's, is extremely reduced: when one operates continuously, under optimal precipitation conditions and under steady process state, the losses of catalyst are of the order of (0.5-1 g)/(1 kg) of end product.

The above illustrated advantages are particularly evident when one operates under conditions of low alcohol:glucose ratios; operating under these conditions is desirable, because it make it possible the volumes of alcohol which are necessary for the reaction to be reduced, with advantages being thereby obtained from the financial, processing safety (alcohols are flammable) and overall reactor dimensions, to be obtained; furthermore, as said in the introductory section, a high ratio of alcohol:glucose leads to APG's with a low average value of n, with the range of product being limited to just a fraction of the possible products.

For a better understanding of the present invention, in the following some examples are reported for merely illustrative purposes, and in no way said examples shall be construed as being limitative of the purview of the same invention.

EXAMPLE 1

90 g of anhydrous glucose (0.5 mols) and 500 g of LIAL 123 (2.56 mols; LIAL 123 products are a blend of linear and branched $C_{12}$–$C_{13}$ oxoalcohols with average molecular weight 195) are charged to a flask of 1 liter of capacity, equipped with stirrer, thermometer and distillation head; the molar ratio of alcohol:glucose is 5.13. The mixture is heated up to 115° C. and 1.147 g is added of 2,4,6-triisopropylbenzene sulfonic acid (0.00404 mols, with a molar ratio of catalyst:glucose of 0.00808), The flask is connected with a vacuum pump and the internal pressure of the system is decreased down to about 20 $mm_{Hg}$. The reaction is continued, at constant temperature and under vacuum, until glucose is completely converted (about 7 hours), with formed water being collected by means of a trap kept at −80° C. A solution is obtained which is clear and nearly colourless. The total content of polyglucose in the end reaction mixture is 0.7 g, corresponding to a polyglucose percent content, based on added glucose, of 0.86%.

EXAMPLE 2

An amount of 200 g of LIAL 123 (1.026 mols) and 90 g of anhydrous glucose (0.5 mols) are charged to the same equipment as of Example 1. The mixture is heated up to 115° C. and 0.546 g of 2,4,6-triisopropyl benzenesulfonic acid (0.0019 mols) is added. The process is carried out as disclosed in Example 1, under 20 $mm_{Hg}$, and with water stripping, with a molar ratio of alcohol:glucose of 2.05 and a molar ratio of catalyst:glucose of 0.0038. The reaction is allowed to continue under constant conditions until the complete conversion of glucose is reached (about 7 hours). At reaction end, the mixture of products is slightly yellow and hazy, but is perfectly fluid at room temperature. After neutralization with an equivalent amount of NaOH, the mass is distilled at 170°–180° C., under a vacuum of 0.1 $mm_{Hg}$, on a LEYBOLD-HAEREUS model KDL1 Thin layer Evaporator. The residue, 122 g, has a good fluidity and flows along the walls of the evaporator. The total content of polyglucose is 4.7 g, corresponding to a conversion rate of initial glucose to polyglucose of 5.8%.

EXAMPLE 3

The process is carried out as in Example 2, by using dodecanol instead of LIAL 123, with an alcohol:glucose ratio of 2.05:1. The reaction is caused to proceed for 7 hours at 110° C., and at reaction end 1.3 g of polyglucose is obtained, with an 1.6% conversion rate of initial glucose into polyglucose.

EXAMPLE 4 (Comparison Example)

The process is carried out as in Example 1, but using, as the catalyst, 0.767 g of p-toluenesulfonic acid monohydrate (0.00404 mols). The reaction temperature is decreased, relatively to Example 1, down to 108°–109° C., in order to get approximately the same H₂O development rate and the same reaction time (7 hours). At the end of the reaction, the reaction mass is more deeply colored, and is much hazier and more viscous than as obtained from the test of Example 1. The total content of polyglucose is 16.5 g, corresponding to a conversion to polyglucose of 20.4% of glucose added as reactant.

EXAMPLE 5 (Comparison Example)

The process is carried out as in Example 2, using, as catalyst, 0.365 g of p-toluenesulfonic acid monohydrate (0.0019 mols). The temperature is kept at 109°–110° C., and the reaction time is 7 hours At reaction end, the product mixture is much more coloured, hazier and viscous than as obtained from the test of Example 2. When is cooled down to room temperature, this mixture appears as a solid mass. The total polyglucose content is 29.6 g, corresponding to a conversion to polyglucose of 36.5% of glucose. It was not possible to distil this mixture under vacuum, as in the preceding example, because the reaction product, owing to its poor fluidity, does not flow along the walls of the thin-layer evaporator, fouling the same walls.

EXAMPLE 6 (Comparison Example)

The process is carried out as in Example 5, however using dodecanol instead of LIAL 123, with a ratio of alcohol:glucose of 2.05:1. The reaction time is 7 hours at a temperature of approximately 105° C. At reaction end, the polyglucose content is 12.8 g, corresponding to a 15.8% conversion rate of initial glucose to polyglucose.

The results of the tests of Examples 1 through 6 are summarized in Table I. From said table, one may see how the polyglucose content in the reaction mixture, and, in particular, the percent conversion rate of initial glucose to polyglucose vary as a function of the ratio of alcohol:glucose reactants and of the type of alcohol used (branched, LIAL; linear, dodecanol): the amount of polyglucose increases with decreasing ratio of alcohol:glucose (reference is made to the comparison between tests of Examples 1 and 2) and when branched alcohols are used instead of linear alcohols (reference is made to the comparison between the tests of Examples 2 and 3 and of Examples 5 and 6); these characteristics of the reaction of formation of APG's render industrially useless the catalysts known from the prior art when one wishes to operate at low alcohol:glucose ratios or with branched alcohols; viceversa, the catalysts according to the present invention, which lead to a low conversion rate to polyglucose, make it possible the process to be carried out with branched alcohols (or their blends) and with low alcohol:glucose ratios.

TABLE I

| EXAMPLE | CATALYST | ALCOHOL | ALCOHOL:GLUCOSE (mol) | POLYGLUCOSE % based on initial glucose |
|---|---|---|---|---|
| 1 | 2,4,6-triisopropyl-benzenesulfonic acid | LIAL 123 | 5.13 | 0.86 |
| 2 | 2,4,6-triisopropyl-benzenesulfonic acid | LIAL 123 | 2.05 | 5.8 |
| 3 | 2,4,6-triisopropyl-benzenesulfonic acid | $CH_3-(CH_2)_{11}-OH$ | 2.05 | 1.6 |
| 4 (Comparison Example) | p-toluenesulfonic acid | LIAL 123 | 5.13 | 20.4 |
| 5 (Comparison Example) | p-toluenesulfonic acid | LIAL 123 | 2.05 | 36.5 |
| 6 (Comparison Example) | p-toluenesulfonic acid | $CH_3-(CH_2)_{11}-OH$ | 2.05 | 15.8 |

EXAMPLE 7

This example relates to the continuous process.

To the same equipment as of Example 1, 200 g of Alchem 123 (a blend of linear $C_{12}$–$C_{13}$ alcohols) and 90 g of glucose (0.5 mols) are added. The mixture is heated at 115° C.; 1 g of catalyst of Example 1 is added. By operating under a vacuum of 20 $mm_{Hg}$ and with water stripping, the reaction is allowed to continue until the complete conversion of glucose is reached (about 4.5 hours), At reaction end, by operating at 50°–60° C. with stirring, 800 ml of acetone is added dropwise to the reaction mixture, during 15 minutes, thus causing the produced APG's to precipitate. The precipitation mixture is cooled down to 20° C. and then is filtered. The filter cake is washed twice with acetone and then is dried at 60° C. under vacuum. The acetone solution is concentrated to dryness, under vacuum, at 80° C. The residue is admixed with 25 g of fresh alcohol and 90 g of glucose, and then is charged once more to the reaction flask at 115° C. and under vacuum, until glucose conversion is complete (about 4 hours). The cycle was repeated 6 times, for a total of 7 reaction cycles, with no further additions of catalyst. At each cycle, from 108 to 110 g of APG's is produced. At the end, the catalyst loss is of about 4%. The product, obtained by combining all of the product fractions recovered from the 7 cycles, displays the following composition:

| Alkylmonoglucosides | 15–20% |
|---|---|
| Alkyldiglucosides | 25–30% |
| Higher alkylglucosides | 45–55% |
| Polyglucose | 3–5% |
| Free alcohol | 0.5–1% |

The average oligomerization degree (n) is 3. The number of cycles can be increased at will, provided that the catalyst is made up every about 10 cycles and the reaction mixture is decoloured every about 3 cycles, by adding, according to as known from the prior art, small amounts of hydrogen peroxide.

The process can be rendered completely continuous by operating with a plurality of reactors in cascade or with a tubular reactor.

We claim:

1. A process for preparing an alkylpolyglycoside of the formula (I);

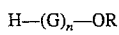 (I)

wherein R is a linear or branched, saturated or unsaturated alkyl radical having from 8 to 20 carbon atoms;
G is a pyranoside or furanoside;
n is an integer from 1 to 5;
said process comprising reacting an alcohol with a monosaccharide, an alkylglycoside, or a compound capable of generating in situ a monosaccharide, in the presence of a sulfonic acid catalyst, wherein the molar ratio of sulfonic acid catalyst and monosaccharide is 0.001 to 0.1 and the molar ratio alcohol to monosaccharide is 1.5 to 3.3;
wherein said sulfonic acid catalyst is of the formula (II):

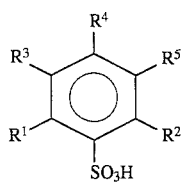 (II)

wherein $R^1$ and $R^2$, the same or different can be:
an alkyl radical having from 1 to 4 carbon atoms;
a halogen selected from the group consisting of Cl, Br and I;
a residue selected from the group consisting of $—OR^6$, $—SR^7$, $—COOR^8$ moieties, wherein $R^6$, $R^7$ and $R^8$ are alkyl residues having from 1 to 4 carbon atoms;
end in which $R^3$, $R^4$ and $R^5$, the same or different, can be hydrogen or any of the meanings as defined above for $R^1$ and $R^2$;
or said sulfonic acid catalyst is of the formula (III):

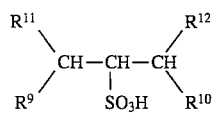 (III)

wherein $R^9$, $R^{10}$, $R^{11}$ and $R_{13}$, the same or different, can be an alkyl radical having from 1 to 4 carbon atoms;
a halogen selected from the group consisting of Cl, Br and I;
a residue selected from the group consisting of $—OR^6$, $—SR^7$, $—COOR^8$ moieties, wherein $R^6$, $R^7$ and $R^8$ are alkyl residues having from 1 to 4 carbon atoms;
and, optionally, $R^{11}$ and $R^{12}$ form, when taken together, a substituted or unsubstituted alkylenic residue having from 2 to 4 carbons.

2. The process of claim 1, wherein said sulfonic acid catalyst is of the formula (II).

3. The process of claim 1, wherein said sulfonic acid catalyst is of the formula (III).

4. The process of claim 1, wherein said sulfonic acid catalyst is 2,4,6-triisopropylbenzenesulfonic acid.

5. The process of claim 1, wherein said sulfonic acid catalyst is 2,4,6-triisobutylbenzenesulfonic acid.

6. The process of claim 1, wherein said sulfonic acid catalyst is 2,4,6-triisopropylbenzenesulfonic acid.

7. The process of claim 1, wherein said sulfonic acid catalyst is 2,2,6,6-tetraisopropyl-cyclohexanesulfonic acid.

8. The process according to claim 1, in which the molar ratio of the sulfonic acid catalyst and glucose is 0.001 to 0.1.

9. The process according to claim 8, in which the molar ratio of the sulfonic acid catalyst and glucose is 0.002 to 0.01.

10. The process according to claim 1, in which the molar ratio of alcohol to monosaccharide is 1 to 7.

11. The process according to claim 10, in which the molar ratio of alcohol to monosaccharide is 1.5 to 3.3.

12. The process according to claim 1, in which the reaction temperature is 110° to 130° C.

* * * * *